(12) United States Patent
Hourmand et al.

(10) Patent No.: US 9,352,089 B2
(45) Date of Patent: May 31, 2016

(54) AUTO-INJECTOR

(75) Inventors: Yannick Hourmand, Cambridgeshire (GB); Timothy Donald Barrow-Williams, St Albans (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 13/807,140

(22) PCT Filed: Jun. 27, 2011

(86) PCT No.: PCT/EP2011/060730
§ 371 (c)(1),
(2), (4) Date: Aug. 13, 2013

(87) PCT Pub. No.: WO2012/000942
PCT Pub. Date: Jan. 5, 2012

(65) Prior Publication Data
US 2013/0317446 A1 Nov. 28, 2013

(30) Foreign Application Priority Data
Jun. 28, 2010 (EP) .................................. 10167487

(51) Int. Cl.
*A61M 5/20* (2006.01)
*A61M 5/315* (2006.01)
(Continued)

(52) U.S. Cl.
CPC ......... *A61M 5/2033* (2013.01); *A61M 5/31511* (2013.01); *A61M 5/326* (2013.01); *A61M 5/46* (2013.01); *A61M 2005/206* (2013.01); *A61M 2005/208* (2013.01)

(58) Field of Classification Search
CPC . A61M 5/3243; A61M 5/3219; A61M 5/322; A61M 5/3221; A61M 5/3202; A61M 5/31535; A61M 5/31583; A61M 5/1454; A61M 2005/31508; A61M 2005/206; A61M 2005/208; A61M 5/2033; A61M 5/31511; A61M 5/326; A61M 5/46
USPC .................. 604/135–137, 187, 192, 196–198
See application file for complete search history.

(56) References Cited

U.S. PATENT DOCUMENTS 5,042,977 A * 8/1991 Bechtold et al. .............. 604/134
5,267,963 A 12/1993 Bachynsky
6,270,479 B1 * 8/2001 Bergens et al. ..... A61M 5/2033
604/156

(Continued)

FOREIGN PATENT DOCUMENTS

WO 2009062508 A1 5/2009
WO 2009081103 A1 7/2009

*Primary Examiner* — Quynh-Nhu H Vu
(74) *Attorney, Agent, or Firm* — Fish & Richardson P.C.

(57) ABSTRACT

An auto-injector comprising a housing arranged to contain a syringe. The syringe is slidably arranged with respect to the housing, a spring capable of pushing a needle from a covered position into an advanced position, operating the syringe to supply a dose of medicament, and retracting the syringe into a covered position and an activator. The spring is arranged to be grounded in the housing for advancing the needle and for injecting the dose of medicament. The drive spring grounded in the housing switched to its proximal end for retracting the syringe. An interlock sleeve telescoped within the housing. The activator comprises a trigger, wherein the trigger button is locked, thereby preventing actuation when the interlock sleeve is in its proximal position in an as delivered state and wherein translation of the interlock sleeve unlocks the trigger button so as to allow actuation.

12 Claims, 7 Drawing Sheets

(51) Int. Cl.
*A61M 5/32* (2006.01)
*A61M 5/46* (2006.01)

(56) References Cited

U.S. PATENT DOCUMENTS

| | | | |
|---|---|---|---|
| 7,361,160 B2* | 4/2008 | Hommann et al. | 604/198 |
| 7,445,613 B2* | 11/2008 | Hommann | A61M 5/31553 604/187 |
| 7,717,877 B2 | 5/2010 | Lavi et al. | |
| 7,976,514 B2* | 7/2011 | Abry et al. | A61M 5/2033 604/110 |
| 2002/0095120 A1* | 7/2002 | Larsen et al. | A61M 5/2033 604/187 |
| 2005/0261634 A1* | 11/2005 | Karlsson | 604/197 |
| 2009/0275916 A1* | 11/2009 | Harms et al. | 604/506 |
| 2010/0094214 A1* | 4/2010 | Abry et al. | A61M 5/20 604/110 |
| 2010/0292653 A1* | 11/2010 | Maritan | A61M 5/2033 604/198 |
| 2011/0213314 A1* | 9/2011 | Guillermo | A61M 5/2033 604/198 |
| 2011/0218500 A1* | 9/2011 | Grunhut et al. | A61M 5/2033 604/228 |
| 2011/0245770 A1* | 10/2011 | Carrel et al. | A61M 5/326 604/117 |

* cited by examiner

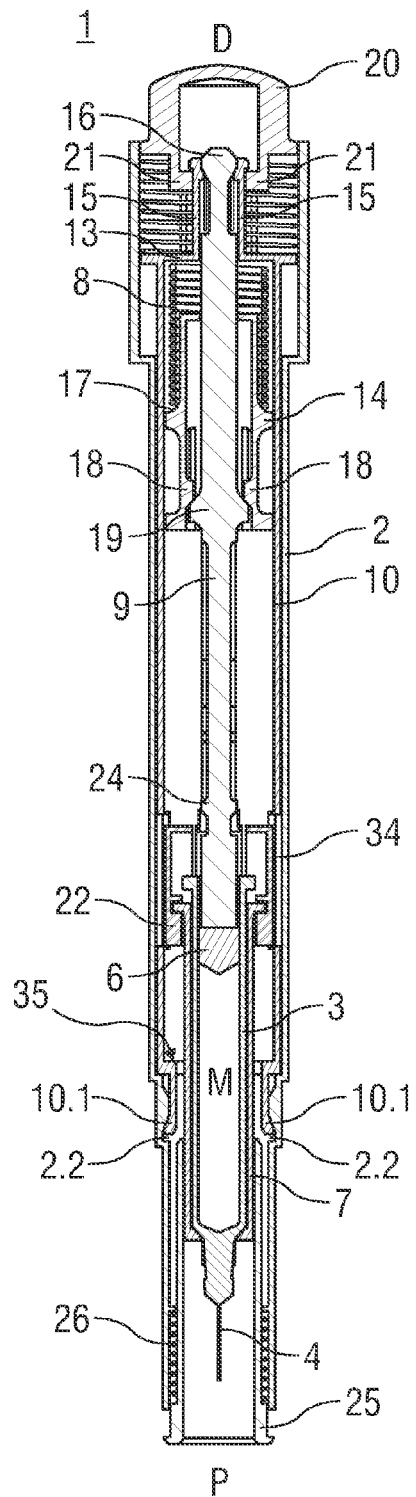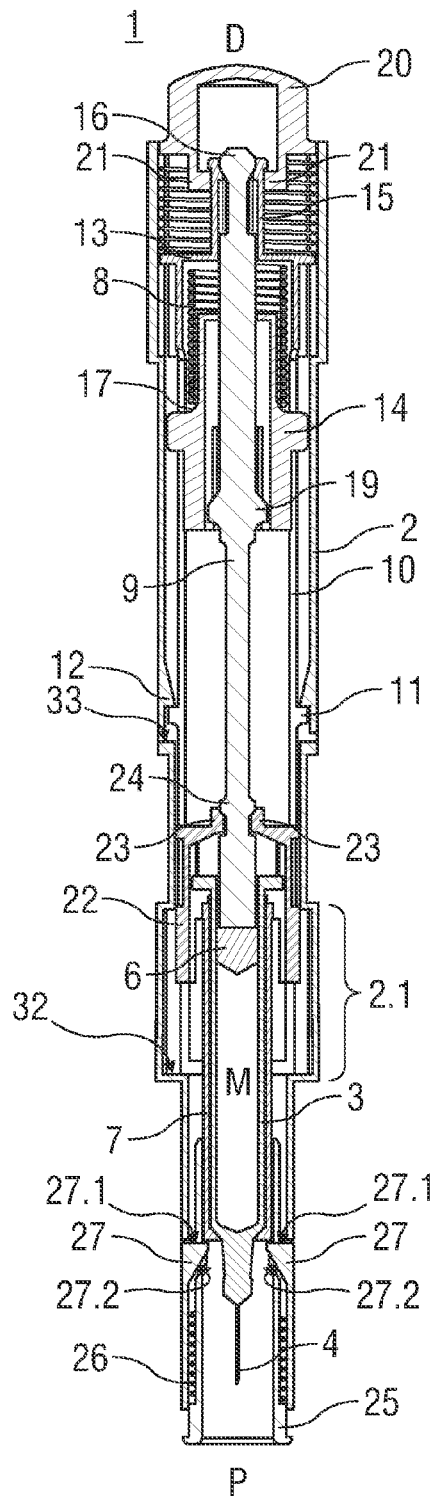
FIG 1A
FIG 1B

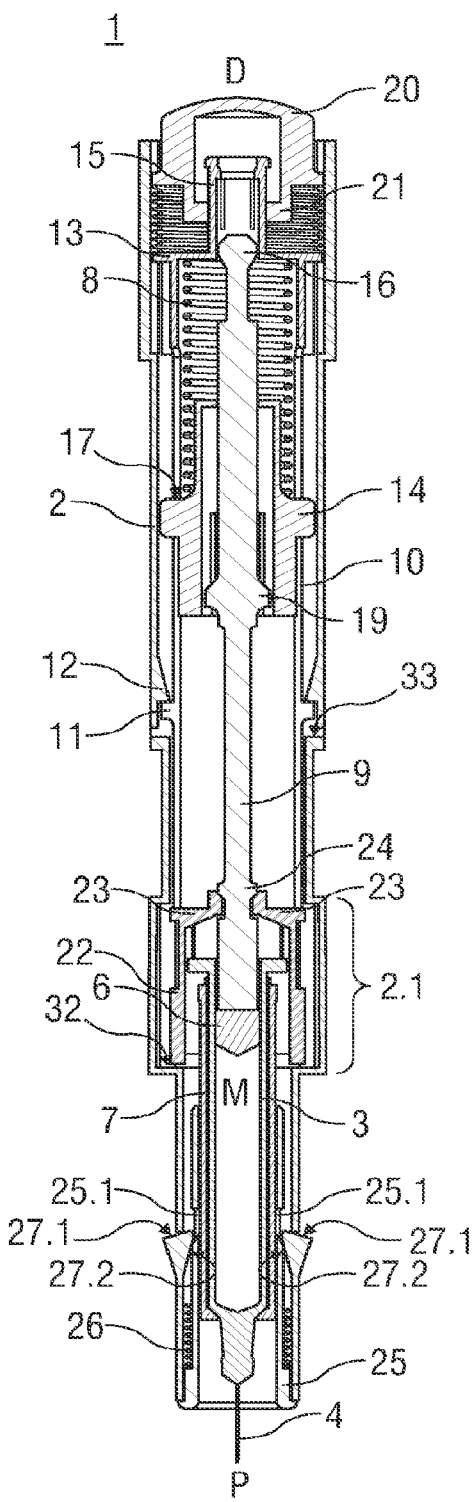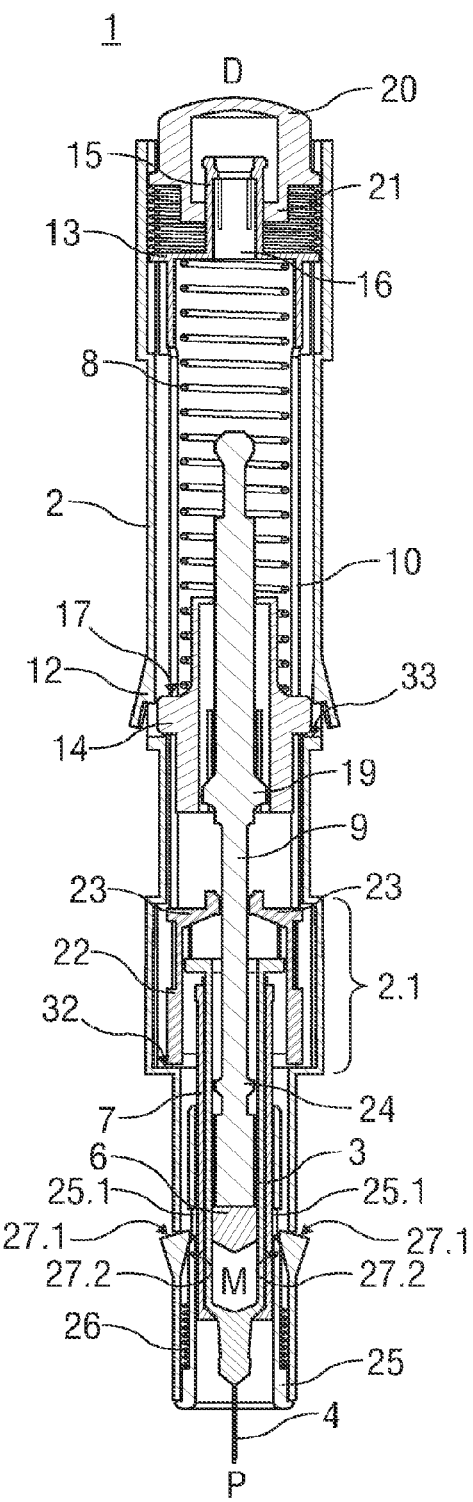
FIG 2C                    FIG 2D

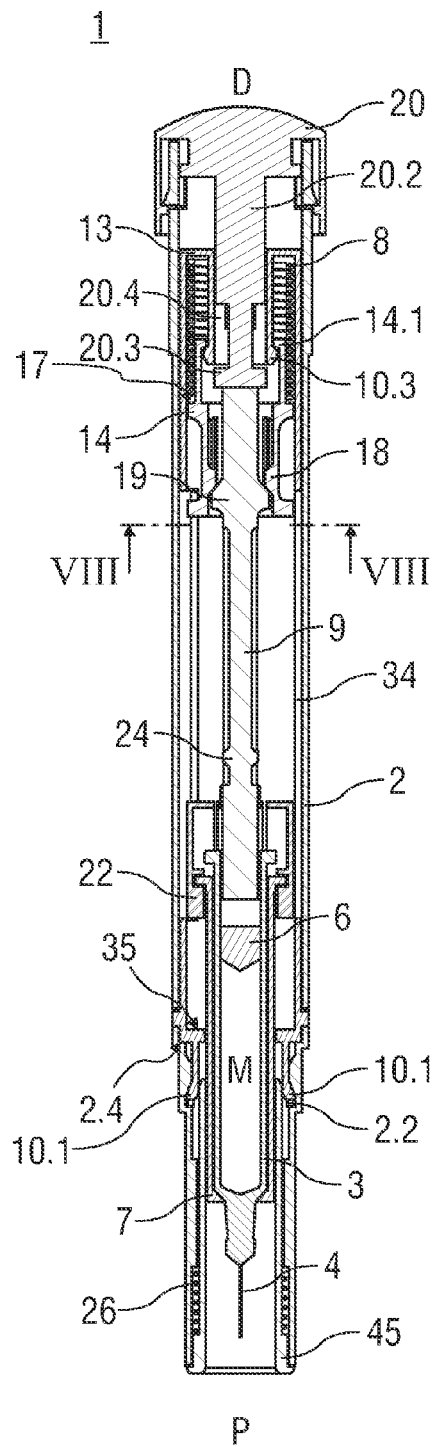
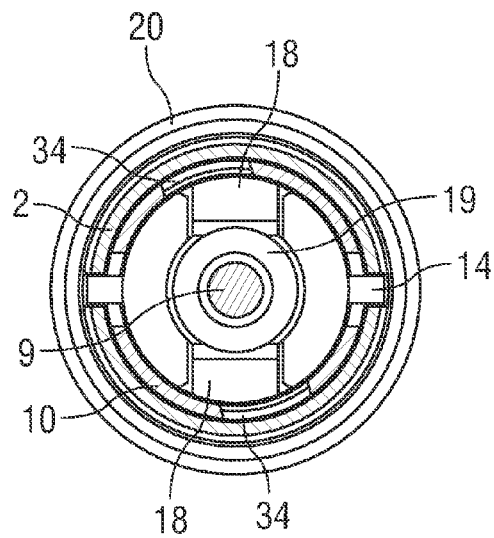
FIG 8
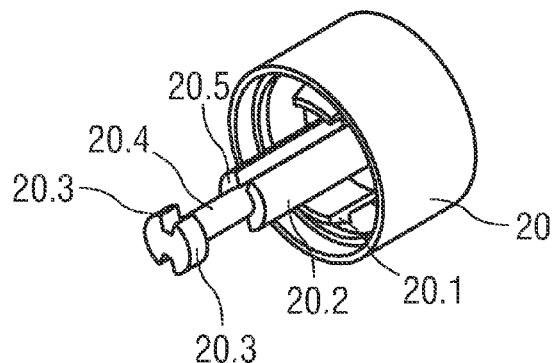
FIG 9
FIG 7

AUTO-INJECTOR

CROSS REFERENCE TO RELATED APPLICATIONS

The present application is a U.S. National Phase application pursuant to 35 U.S.C. §371 of International Application No. PCT/EP2011/060730 filed Jun. 27, 2011, which claims priority to European Patent Application No. 10167487.7 filed Jun. 28, 2010. The entire disclosure contents of these applications are herewith incorporated by reference into the present application.

TECHNICAL FIELD OF INVENTION

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

The spring means is a single compression spring arranged to be grounded at a distal end in the housing for advancing the needle and for injecting the dose of medicament via a plunger and wherein the compression spring is arranged to have its ground in the housing switched to its proximal end for retracting the syringe.

SUMMARY

It is an object of the present invention to provide an improved auto-injector with a means for reducing the risk of inadvertent triggering.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient.

According to the invention, an auto-injector for administering a dose of a liquid medicament comprises:

an elongate housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing, spring means capable of, upon activation:
  pushing the needle from a covered position inside the housing into an advanced position through the orifice and past the proximal end,
  operating the syringe to supply the dose of medicament, and
  retracting the syringe with the needle into the covered position after delivering the medicament, activating means arranged to lock the spring means in a pressurized state prior to manual operation and capable of, upon manual operation, releasing the spring means for injection.

According to the invention the spring means is a single drive spring in the shape of a compression spring arranged to be grounded at a distal end in the housing for advancing the needle and for injecting the dose of medicament. The force of the drive spring is forwarded to the needle and/or the syringe via a plunger. The drive spring is arranged to have its ground in the housing switched to its proximal end for retracting the syringe when the injection of the medicament is at least nearly finished.

The single drive spring is used for inserting the needle, fully emptying the syringe and retracting the syringe and needle to a safe position after injection. Thus a second spring for withdrawing the syringe and needle, which is a motion with an opposite sense compared to advancing the syringe and injecting the dose, is not required. While the distal end of the drive spring is grounded the proximal end moves the syringe forward for inserting the needle and carries on to the injection by pushing on the stopper. When the injection is at least nearly finished the drive spring bottoms out at its proximal end, resulting in the proximal end being grounded in the housing. At the same time the distal end of the drive spring is released from its ground in the housing. The drive spring is now pulling the syringe in the opposite direction.

According to the invention an interlock sleeve is telescoped in the proximal end of the housing, the interlock sleeve translatable in longitudinal direction between a proximal position and a distal position and biased in proximal direction in a manner to protrude from the housing in the proximal position. The activating means comprises a trigger button arranged at the distal end of the auto-injector. The trigger button is locked, thereby preventing actuation when the interlock sleeve is in its proximal position in an as delivered state. Translation of the interlock sleeve unlocks the trigger button so as to allow actuation.

This results in an auto-injector with a sequenced operation. In the as delivered state the interlock sleeve is in its proximal position protruding from the proximal end of the housing. The syringe and needle are in their retracted position. In order to trigger an injection the auto-injector has to be pressed with its proximal end against an injection site, e.g. a patient's skin in a manner to translate the interlock sleeve in distal direction into the housing. This translation allows the trigger button to be actuated for eventually releasing the drive spring and start an injection cycle. The probability for inadvertent operation of the auto-injector decreases due to the requirement of two sequenced user actions, pressing the auto-injector against the injection site and operating the activating means.

The auto-injector according to the invention has a particularly low part count compared to most conventional auto-injectors. The use of just one drive spring reduces the amount of metal needed and thus consequently reduces weight and manufacturing costs.

The connection from the interlock sleeve at the proximal end to the trigger button at the distal end may be established by the interlock sleeve or a part of it extending through the entire auto-injector to the trigger button. This may result in a complex design since interaction with the mechanisms for advancing the needle, injecting the dose and retracting the needle have to be avoided. In a preferred embodiment the interlock sleeve is coupled to the plunger for joint axial translation in the as delivered state. A distal end of the plunger is arranged to interact with the trigger button in a manner to lock and/or unlock it. Extending the interlock sleeve to the distal end with the aforesaid drawbacks may thus be avoided. Furthermore the auto-injector may be designed less bulky.

A tubular syringe carrier may be arranged for holding the syringe and supporting it at its proximal end. Supporting the syringe at the proximal end is preferred over support at the finger flanges since the finger flanges are more frangible under load while the proximal or front end of the syringe is more robust. The syringe and the syringe carrier are arranged for joint axial translation. The syringe carrier is telescoped in the interlock sleeve. The syringe may be arranged for joint axial movement with a syringe holder which is slidably arranged in the retraction sleeve. The syringe holder is provided with at least one resilient syringe holder arm (preferably two) arranged distally, the syringe holder arms having a respective inclined surface for bearing against a second shoulder, which may be arranged at the plunger proximally from a first shoulder. The syringe holder arms are supportable by an inner surface of the housing in order to prevent them from being flexed outward. Thus, when the trigger button is pressed the spring force forwarded by the plunger does not yet press against the stopper but against the syringe for forwarding it. Consequently, a so called wet injection is avoided, i.e. the liquid medicament is not leaking out of the hollow needle before the needle is inserted. A widened portion is provided in the housing for allowing the syringe holder arms to flex outwards when the syringe holder has nearly reached a maximum proximal position thus allowing the second shoulder to slip through the syringe holder arms and to switch load of the drive spring from the syringe to the stopper. This allows for defining the moment to start injecting the medicament. In its proximal position the interlock sleeve is arranged to be coupled to the syringe carrier in the syringe's retracted position. As the interlock sleeve and the syringe are coupled for joint axial movement the syringe and needle cannot advance even if the spring means were inadvertently released or the if the auto-injector were vigorously shaken. Thus the needle remains in its covered position. The interlock sleeve in its distal position is arranged to allow decoupling of the syringe carrier. The actual decoupling occurs upon release of the drive spring and the resulting translation of the syringe carrier in proximal direction with the interlock sleeve being held in distal position by the injection site. The syringe is now translated so as to move the needle into its advanced position for piercing the patient's skin. In the as delivered state the interlock sleeve, the syringe carrier, the syringe, the syringe holder and the plunger are floating as a single part in the auto-injector.

The auto-injector may also be embodied without the syringe holder. In this case the interlock sleeve would be coupled to the plunger via the syringe carrier, the syringe and the stopper in the as delivered state.

Decoupling the interlock sleeve from the syringe carrier may be achieved by at least one resilient clip provided in the interlock sleeve. A respective recess for each clip is arranged in the syringe carrier so as to allow the clip to engage the syringe carrier. The clip is outwardly supported by the housing in the as delivered state thus preventing it from disengaging the syringe carrier. At least one ramp is arranged to disengage the clip from the recess when the syringe carrier and the interlock sleeve are pushed against each other in longitudinal direction with the interlock sleeve in its distal position.

A retraction sleeve may be axially movable arranged in the housing, wherein the drive spring is arranged inside the retraction sleeve with its distal end bearing against a distal end face and with its proximal end bearing against a thrust face of a decoupling member. In the as delivered state the position of the trigger button, the retraction sleeve and the decoupling member may be as follows:

The retraction sleeve is in its proximal position and engaged with the decoupling member so as to prevent release of the drive spring.

The trigger button is in its distal position preventing disengagement of the retraction sleeve from the decoupling member.

The trigger button is latched to the retraction sleeve so as to prevent actuation of the trigger button.

The plunger may be arranged to de-latch the trigger button from the retraction sleeve upon translation of the plunger in distal direction so as to allow actuation of the trigger button. At least one ramp may be provided for disengaging the retraction sleeve from the decoupling member under load of the drive spring when the trigger button is actuated.

A central shaft may extend from the trigger button in proximal direction towards the plunger, the central shaft having a shoulder for abutting against at least one resilient clip arranged on the retraction sleeve in the as delivered state. At least one bar may extend distally from the distal end of the plunger, the bar arranged to disengage the resilient clip from the central shaft upon translation of the plunger in distal direction.

At least one catch may be arranged on the retraction sleeve for engaging a respective catch on the decoupling member in the as delivered state. At least one dog on the trigger button is arranged to support one of the catches prior to actuation of the trigger button so as to prevent disengagement of the catches. The dog is arranged to be translated upon actuation of the trigger button so as to no longer support the catch and allow disengagement of the catches under load of the drive spring in order to start the injection cycle.

At least one resilient decoupling arm (preferably two) is arranged at the decoupling member. The decoupling arms exhibit inner ramped surfaces bearing against a first shoulder of the plunger in proximal direction. The resilient decoupling arms are supportable by an inner wall of the retraction sleeve in order to prevent the decoupling arms from being flexed outward and slip past the first shoulder. In this state the plunger may be pushed in proximal direction by the decoupling member pushing against the first shoulder in order to insert the needle and inject the dose. At least one aperture is arranged in the retraction sleeve allowing the decoupling arms to be flexed outward by the first shoulder thus allowing the first shoulder to slip through the decoupling arms in proximal direction. This may happen when the injection is at least nearly finished. The decoupled plunger allows the syringe and needle to be retracted since it is no longer bearing against the decoupling member.

In the as delivered state the first shoulder is preferably situated a small distance proximally from the ramped surface of the decoupling arm. The plunger is thus allowed to be translated this distance in distal direction without moving the decoupling member.

It is desirable to trigger the retraction of the needle when the contents of the syringe have been entirely delivered to the patient, i.e. when the stopper has bottomed out in the syringe. Automatically triggering the retraction when the stopper exactly reaches the end of its travel is a problem due to tolerances when manufacturing the syringe and stopper. Due to these tolerances the position of the stopper relative to the means triggering retraction at the end of its travel is not repeatable. Consequently, in some cases the stopper would prematurely bottom out so the retraction would not be triggered at all. In other cases the retraction would be triggered before the stopper bottomed out so residual medicament would remain in the syringe.

The retraction could automatically be triggered a certain amount of time or travel before the stopper bottoms out in the syringe. However this reliable retraction would be traded off for residual medicament in the syringe.

Thus, in a preferred embodiment the interlock sleeve is furthermore arranged to prevent release of the distal ground of the drive spring when in the distal position. This means, the drive spring remains distally grounded as long as the auto-injector is kept pressed against the injection site so the needle retraction can only start when the auto-injector is removed from the injection site and the interlock sleeve consequently returns into its proximal position and thus releases the distal ground. Full delivery of the medicament and reliable retraction are thus achieved by waiting for the user action of removing the auto-injector from the injection site.

For this purpose the interlock sleeve may be engaged to the retraction sleeve by at least one resilient wedge arranged at the proximal end of the retraction sleeve. The housing has a respective recess for accommodating the resilient wedge when the retraction sleeve is in its proximal position. The interlock sleeve in its distal position may be arranged to support the resilient wedge from inside so as to prevent it from translating in distal direction. Thus, when the interlock sleeve is pressed against the injection site, the retraction sleeve is kept from retracting. Only after removal of the auto-injector from the injection site and consequent translation of the interlock sleeve into its proximal position the retraction sleeve may translate in distal direction and retract the needle into the housing.

The aperture in the retraction sleeve may extend at least almost to the position of the decoupling arm in the as delivered state up to the decoupling arm's position at the end of dose. The aperture may be arranged to be angularly misaligned with respect to the decoupling arm when the retraction sleeve is in its proximal position so the plunger does not decouple from the decoupling member. The aperture and the retraction sleeve are also arranged to rotate so as to align the aperture with the decoupling arm upon translation of the retraction sleeve out of the proximal position in distal direction so the plunger and decoupling member decouple from each other thus allowing retraction of the plunger, stopper syringe and needle. This embodiment allows for starting the retraction at any point of the injection cycle, even before the end of dose.

The rotation into the aligned position may be achieved by a cam track arranged in the housing and a cam follower in the retraction sleeve. The cam track may be essentially parallel to a longitudinal axis of the auto-injector with a short angled section at its proximal end.

Alternatively the cam track may be arranged in the retraction sleeve and the cam follower in the housing.

Preferably a cap is provided at the proximal end of the housing. A sheet metal clip is attached to the cap for joint axial movement and independent rotation. The sheet metal clip is arranged to extend through an orifice into the interlock sleeve when the cap is attached to the interlock sleeve. The sheet metal clip incorporates at least two barbs snapped into a circumferential notch or behind a shoulder of the protective needle shield. This allows for automatically engaging the sheet metal clip with the protective needle shield during assembly. When the cap is removed from the interlock sleeve in preparation of an injection the protective needle shield is reliably removed without exposing the user too high a risk to injure themselves.

The cap may be attachable to the housing by a screw connection. This allows for a low force removal of the protective needle shield.

The housing may have at least one viewing window for inspecting the syringe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The cap with the sheet metal spring may also be applied with other auto-injectors and injection devices.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limiting of the present invention, and wherein:

FIGS. 1A and 1B are two longitudinal sections of an auto-injector with a single drive spring for advancing a syringe with a needle, injecting a dose of medicament and retracting the syringe and needle, the auto-injector as-delivered, FIGS. 2C and 2D are two longitudinal sections of the auto-injector with a needle in an advanced position, FIG. 7 is a longitudinal section of the auto-injector of FIG. 6, FIG. 8 is a cross section of the auto-injector of FIG. 7 in the section plane VIII-VIII, and FIG. 9 is an isometric detail view of a trigger button.

Corresponding parts are marked with the same reference symbols in all figures.

DETAILED DESCRIPTION

Figure 2A:
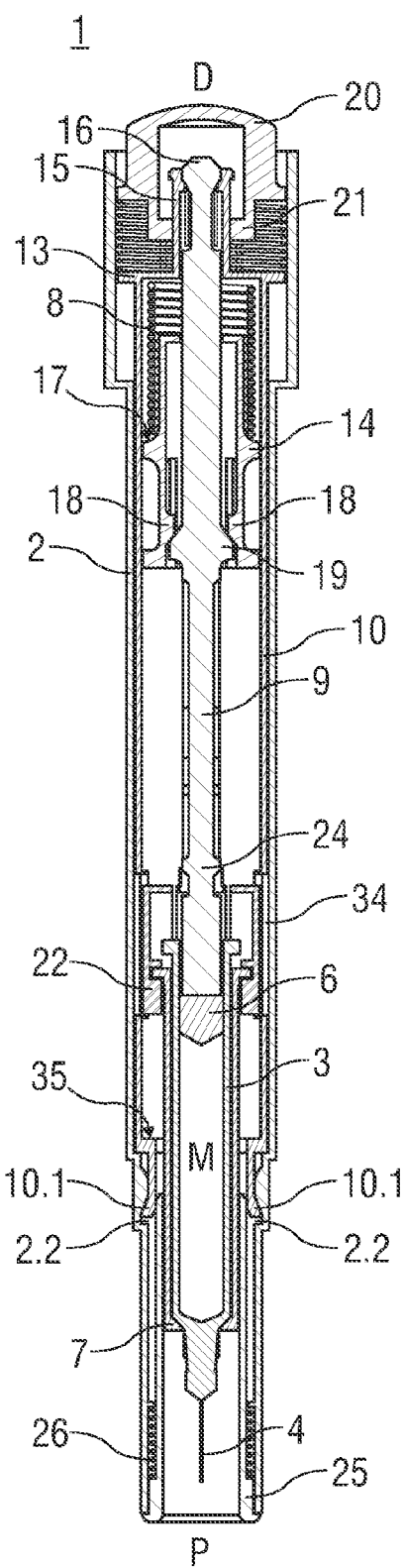
FIGS. 2A and 2B are two longitudinal sections of the auto-injector with a skin interlock sleeve pressed against an injection site.

FIGS. 1A and 1B show two longitudinal sections in different section planes of an auto-injector 1, the different section planes approximately 90° rotated to each other. The auto-injector 1 comprises an elongate housing 2. A syringe 3, e.g. a Hypak syringe, with a hollow needle 4 is arranged in a proximal part of the auto-injector 1. When the auto-injector 1 or the syringe 3 is assembled a protective needle shield may be attached to the needle (not illustrated). A stopper 6 is arranged for sealing the syringe 3 distally and for displacing a liquid medicament M through the hollow needle 4. The syringe 3 is held in a tubular syringe carrier 7 and supported at its proximal end therein. A single drive spring 8 in the shape of a compression spring is arranged in a distal part of the auto-injector 1. A plunger 9 is arranged for forwarding the spring force of the drive spring 8.

Inside the housing 2 a retraction sleeve 10 is slidably arranged. Before the injection is triggered the retraction sleeve 10 is in a maximum proximal position and prevented from moving in distal direction D by means of stops 11 caught behind latches 12 in the housing 2. A distal end of the drive spring 8 bears against an end face 13 of the retraction sleeve 10. Due to the stops 11 and latches 12 the force of the drive spring 8 is thus reacted into the housing 2. The proximal end of the drive spring 8 bears against a decoupling member 14 arranged around the plunger 9. Distally from the end face 13 the retraction sleeve has two or more resilient arms 15 for holding a stud 16 and keeping it from being moved in proximal direction P. The stud 16 is arranged at the distal end of the plunger 9. The stud 16 and the resilient arms 15 have corresponding ramp features for pushing the resilient arms 15 apart in order to allow the stud 16 and the plunger 9 to move in proximal direction P.

The decoupling member 14 comprises a thrust face 17 for bearing against a proximal end of the drive spring 8. Proximally from the thrust face 17 two or more resilient decoupling arms 18 are provided at the decoupling member 14, the decoupling arms 18 having inner ramped surfaces bearing against a first shoulder 19 in the plunger 9 in proximal direction P. The resilient decoupling arms 18 are supported by an inner wall of the retraction sleeve 10 in this situation so they cannot flex outward and slip past the first shoulder 19.

A trigger button 20 is arranged at the distal end D of the auto-injector 1. The trigger button 20 may be pushed in proximal direction P in order to start an injection. As long as the trigger button 20 is not pushed the resilient arms 15 are caught between two or more retainers 21 arranged at the trigger button 20 so the resilient arms 15 cannot flex outward and the stud 16 although proximally biased by the drive spring 8 cannot slip through.

The syringe carrier 7 is engaged for joint axial movement with a syringe holder 22 which is slidably arranged in the retraction sleeve 10. The syringe holder 22 is provided with two or more resilient syringe holder arms 23 arranged distally. The syringe holder arms 23 have a respective inclined surface for bearing against a second shoulder 24 in the plunger 9 arranged proximally from the first shoulder 19. In the initial position shown in FIGS. 1A and 1B, the syringe holder arms 23 are supported by an inner surface of the housing 2 so they cannot flex outward and the second shoulder 24 cannot slip through. In order to support the syringe holder arms 23 at the housing 2 a respective number of apertures are provided in the retraction sleeve 10.

Two resilient wedges 10.1 are arranged at a proximal end of the retraction sleeve 10. The housing 2 has two recesses 2.2 arranged to accommodate the resilient wedges 10.1 when the retraction sleeve 10 is in its proximal position.

A skin interlock sleeve 25 is telescoped in the proximal end P of the housing 2. The syringe carrier 7 in turn is telescoped in the interlock sleeve 25. The interlock sleeve 25 is biased in proximal direction P by an interlock spring 26. Two resilient second latches 27 are arranged in the housing 2 near the proximal end P. In the state as delivered the second latches 27 are relaxed and extend inwardly through respective apertures 25.1 in the interlock sleeve 25 in a manner to prevent the syringe carrier 7 from translating in proximal direction P by the syringe carrier 7 abutting against respective distal faces 27.1 of the second latches 27. The syringe carrier 7, the syringe 3 and the needle 4 can therefore not be forwarded when pushed by the plunger 9.

Figure 2B:
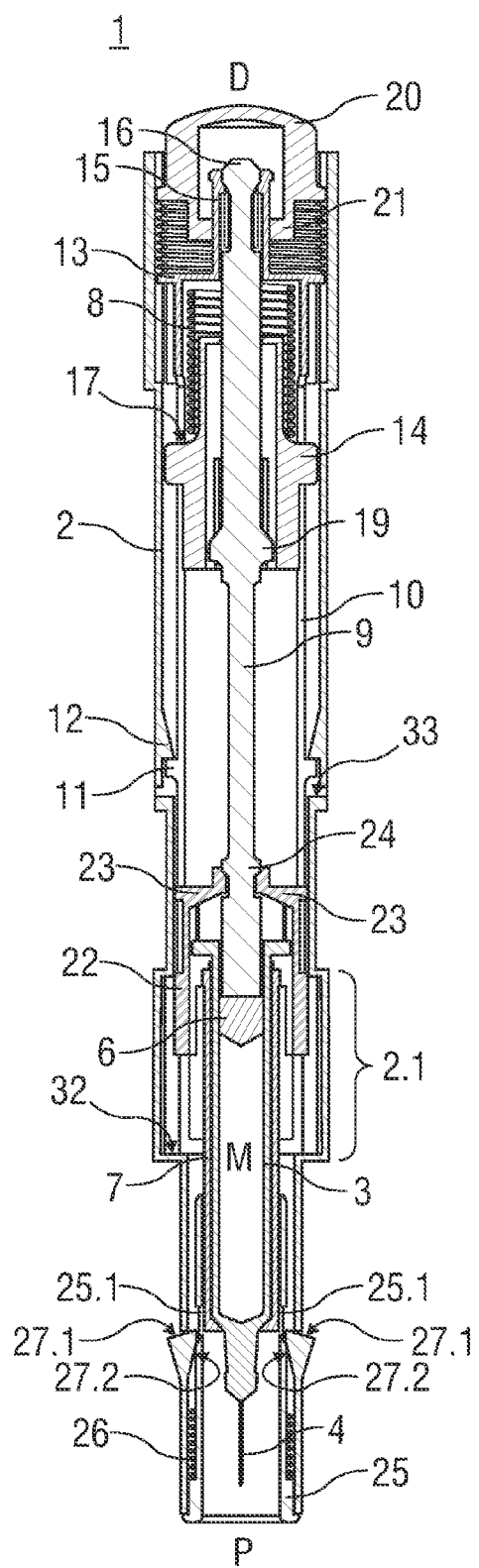

In order to start an injection the auto-injector 1 has to be pressed against the injection site, e.g. a patient's skin. As a result the interlock sleeve 25 translates in distal direction D into the housing 2 (see FIGS. 2A and 2B). A proximal edge of the aperture 25.1 pushes against a proximal ramp 27.2 of the second latch 27 thereby flexing the second latch 27 outwards so the syringe carrier 7 comes clear of the distal faces 27.1 and may now translate in proximal direction P. When translated into the housing 2 as in FIGS. 2A and 2B a distal end of the interlock sleeve 25 supports the resilient wedges 10.1 from inside so they cannot be flexed inwards thus preventing the retraction sleeve 10 from translating in distal direction D.

The trigger button 20 can now be pushed to release the drive spring 8 in order to insert the needle 4 into the injection site and to inject the medicament M, as shown in FIGS. 2C and 2D.

If the auto-injector 1 is removed from the injection site without operating the trigger button 20 the interlock sleeve 25 will translate back into its proximal position under load of the interlock spring 26. The second latches 27 will flex inwards and block the syringe carrier 7 so the auto-injector 1 is in its as delivered state again.

The sequence of operation can be reversed in this embodiment, i.e. the trigger button 20 may be pushed before pressing the auto-injector 1 against the injection site.

When the trigger button 20 is pushed the retainers 21 are pushed in proximal direction P so the resilient arms 15 are allowed to flex outward. Under load of the drive spring 8 the inclined surfaces of the stud 16 force the resilient arms 15 apart until the stud 16 can slip through.

The second shoulder 24 pushes the syringe holder 22, syringe carrier 7 and syringe 3 forward while no load is exerted onto the stopper 6. The hollow needle 4 appears from the proximal end P and is inserted into an injection site, e.g. a patient's skin (see FIGS. 2C and 2D).

The forward movement continues until the syringe holder 22 bottoms out at a first abutment 32 in the housing 2. The travel from the initial position up to this point defines an injection depth, i.e. needle insertion depth.

When the syringe holder 22 has nearly bottomed out the resilient syringe holder arms 23 have reached a widened portion 2.1 of the housing 2 where they are no longer supported by the inner wall of the housing 2. However, since the force required to insert the needle 4 is relatively low the second shoulder 24 will continue to drive forward the syringe holder 22 until proximal travel is halted at the first abutment 32. At this point the syringe holder arms 23 are flexed out by the continued force of the second shoulder 24 and allow it to slip through. Now the plunger 9 no longer pushes against the syringe holder 22 but against the stopper 6 for expelling the medicament M from the syringe 3 and injecting it into or through the patient's skin.

When the stopper 6 has nearly bottomed out in the syringe 3 the decoupling member 14 has reached a position where it pushes against the latches 12 in a manner to decouple the retraction sleeve 10 from the housing 2. Thus the drive spring 8 is no longer grounded with its distal end in the housing 2 by the latches 12. Instead, as soon as the decoupling member 14 has bottomed out at a second abutment 33 the proximal end of the drive spring 8 gets grounded in the housing 2 while its distal end is pulling the retraction sleeve 10 in distal direction D.

Just before the decoupling member 14 decouples the retraction sleeve 10 from the housing 2 the decoupling arms 18 reach an aperture 34 in the retraction sleeve 10 so they are no longer kept from being flexed outward. The decoupling arms 18 are thus pushed outward by the first shoulder 19 pushing against its ramped surfaces so the first shoulder 19 can slip through in distal direction D as soon as the decoupling member 14 has hit the second abutment 33.

Although the latches 12 are disengaged now, the retraction sleeve 10 may not yet slide in distal direction D because of the resilient wedges 10.1 being held in the recess 2.2 between the housing 2 and the interlock sleeve 25 as long as the interlock sleeve 25 is in its distal position by the auto-injector 1 being kept pushed against the injection site.

If the auto-injector 1 is taken away from the injection site the interlock sleeve 25 will return to its proximal position (as in FIGS. 1A and 1B) under load of the interlock spring 26 so the resilient wedges 10.1 are no longer supported from inside. Since the drive spring 8 tries to pull the retraction sleeve 10 in distal direction D, distal ramps of the resilient wedges 10.1 move along proximal ramps of the recesses 2.2 thereby flexing the resilient wedges inwards as the retraction sleeve 10 starts translating in distal direction.

The syringe holder 22 is taken along in distal direction D by the retraction sleeve 10, e.g. by a front face 35. Thus the syringe 3 and needle 4 are retracted into a safe position inside the housing 2, e.g. into the initial position. The plunger 9, no longer bearing against the decoupling arms 18 is pulled back too.

In the embodiment illustrated in FIGS. 1A, 1B, 2A, and 2B, the latches 12 and the stops 11 at the retraction sleeve 10 are not absolutely required. Retraction can be triggered by removal of the auto-injector 1 from the injection site alone. However, the latches 12 and the stops 11 facilitate assembly of the auto-injector 1 and give an initial position to the retraction sleeve 10. Furthermore, the stops 11 as well as lugs on the decoupling member 14 for disengaging the latches 12 and the stops 11 run in a slot 2.6 in the housing 2 thus preventing the retraction sleeve 10 and the decoupling member 14 from rotating.

Figure 3A:
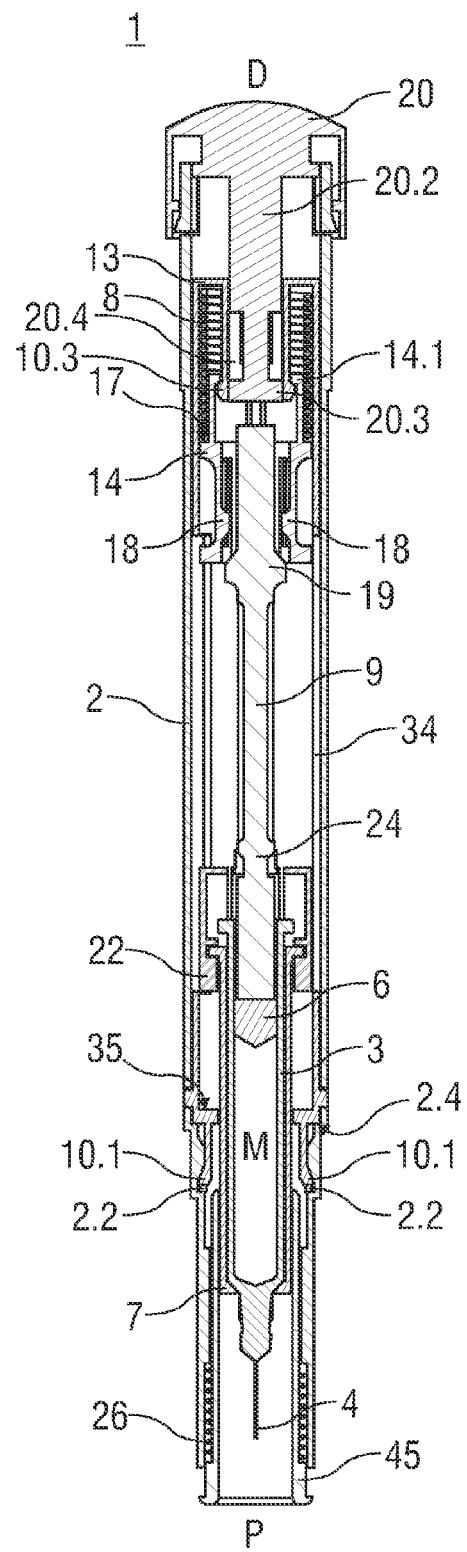
FIGS. 3A and 3B are two longitudinal sections of another auto-injector with a modified trigger button.
Figure 3B:
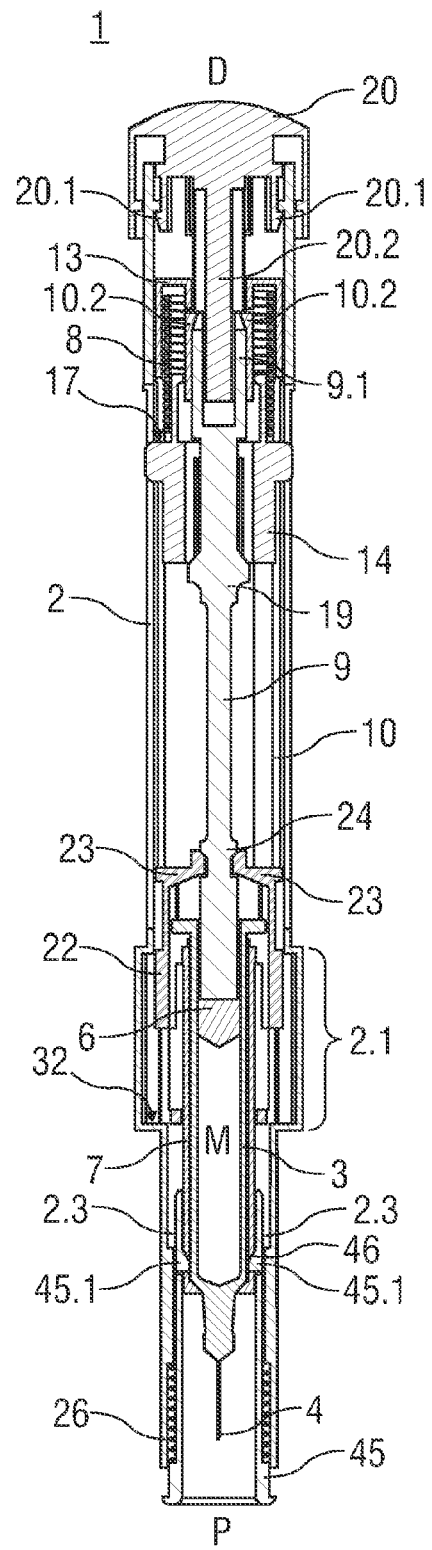

FIGS. 3A and 3B show two longitudinal sections in different section planes of another embodiment of an auto-injector 1, the different section planes approximately 90° rotated to each other. The auto-injector 1 comprises an elongate housing 2. A syringe 3, e.g. a Hypak syringe, with a hollow needle 4 is arranged in a proximal part of the auto-injector 1. When the auto-injector 1 or the syringe 3 is assembled a protective needle shield may be attached to the needle (not illustrated). A stopper 6 is arranged for sealing the syringe 3 distally and for displacing a liquid medicament M through the hollow needle 4. The syringe 3 is held in a tubular syringe carrier 7 and supported at its proximal end therein. A single drive spring 8 in the shape of a compression spring is arranged in a distal part of the auto-injector 1. A plunger 9 is arranged for forwarding the spring force of the drive spring 8.

Inside the housing 2 a retraction sleeve 10 is slidably arranged. Before the injection is triggered the retraction sleeve 10 is in a maximum proximal position abutting against a stop 2.4 in the housing 2. A distal end of the drive spring 8 bears against an end face 13 of the retraction sleeve 10. The proximal end of the drive spring 8 bears against a decoupling member 14 arranged around the plunger 9.

The decoupling member 14 comprises a thrust face 17 for bearing against a proximal end of the drive spring 8. Proximally from the thrust face 17 two or more resilient decoupling arms 18 are provided at the decoupling member 14, the decoupling arms 18 having inner ramped surfaces arranged for bearing against a first shoulder 19 in the plunger 9 in proximal direction P. In the as delivered state in FIGS. 3A and 3B the first shoulder 19 is situated a small distance proximally from the ramped surfaces of the decoupling arms 18. The resilient decoupling arms 18 may be supported by an inner wall of the retraction sleeve 10 for preventing them from being flexed outward and slip past the first shoulder 19. Apertures 34 are provided in the retraction sleeve 10 for allowing the decoupling arms 18 to flex outwards.

A trigger button 20 is arranged at the distal end D of the auto-injector 1. The trigger button 20 is arranged to be pushed in proximal direction P in order to start an injection.

The syringe carrier 7 is engaged for joint axial movement with a syringe holder 22 which is slidably arranged in the retraction sleeve 10. The syringe holder 22 is provided with two or more resilient syringe holder arms 23 arranged distally. The syringe holder arms 23 have a respective inclined surface for bearing against a second shoulder 24 in the plunger 9 arranged proximally from the first shoulder 19. In the initial position shown in FIGS. 3A and 3B, the syringe holder arms 23 are supported by an inner surface of the housing 2 so they cannot flex outward and the second shoulder 24 cannot slip through. In order to support the syringe holder arms 23 at the housing 2 a respective number of apertures are provided in the retraction sleeve 10.

Two resilient wedges 10.1 are arranged at a proximal end of the retraction sleeve 10. The housing 2 has two recesses 2.2 arranged to accommodate the resilient wedges 10.1 when the retraction sleeve 10 is in its proximal position.

A skin interlock sleeve 45 is telescoped in the proximal end P of the housing 2. The syringe carrier 7 in turn is telescoped in the interlock sleeve 45. The interlock sleeve 45 is biased in proximal direction P by an interlock spring 26.

In the as delivered state as shown in FIGS. 3A and 3B, the interlock sleeve 45 is coupled with the syringe carrier 7 by resilient clips 45.1 provided in the interlock sleeve 45. The clips 45.1 are engaged in a respective recess in the syringe carrier 7 and outwardly supported by the housing 2 so they cannot flex outward. Hence, in the state as delivered, the interlock sleeve 45, the syringe carrier 7 with the syringe 3 and the needle 4, the syringe holder 22 and the plunger 9 are coupled for joined axial translation. The recess in the syringe carrier 7 and the clip 45.1 have ramps arranged to flex the clip 45.1 outwards when the syringe carrier 7 and the interlock sleeve 45 are pushed against each other in longitudinal direction.

The syringe carrier 7, the syringe 3 and the needle 4 can therefore not be forwarded when pushed by the plunger 9.

Figure 4:
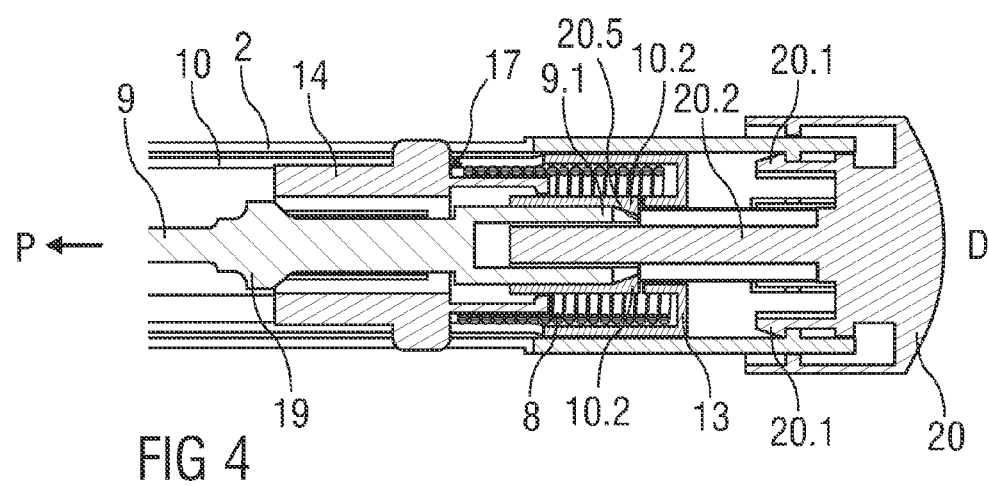
FIG. 4 is a detail view of the trigger button of FIG. 3 prior to actuation.
Figure 5A:
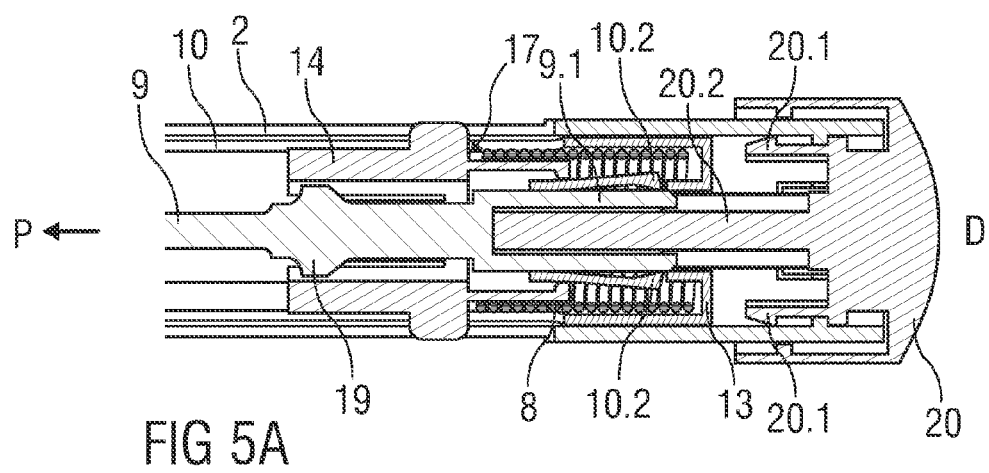
FIGS. 5A and 5B are two detail views of the trigger button of FIG. 3 upon actuation.
Figure 5B:
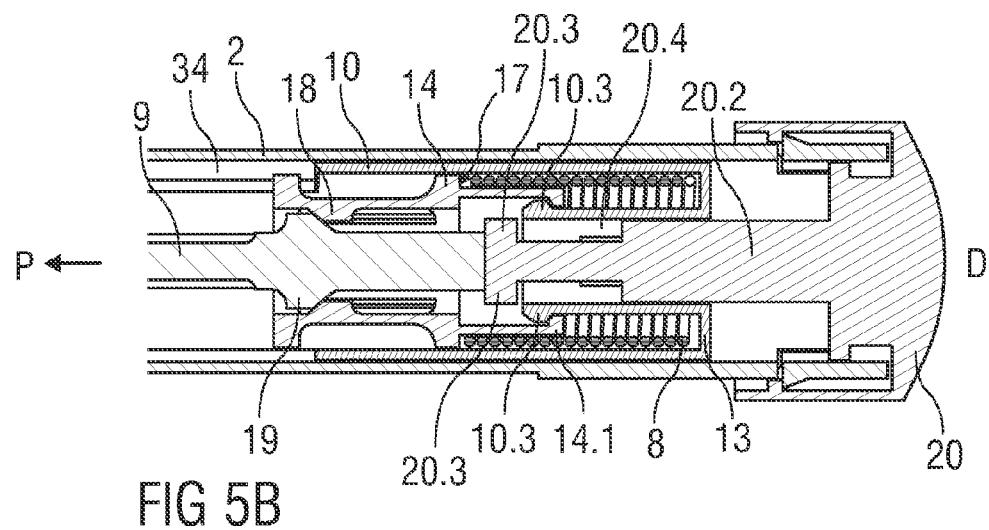

The trigger button 20 is secured on the housing 2 by means of clips 20.1 so it cannot translate in distal direction D further than shown in FIG. 4. A central shaft 20.2 extends from the trigger button 20 in proximal direction towards the plunger 9. Another set of resilient clips 10.2 are arranged on the retraction sleeve 10 proximally from the end face 13 inside the drive spring 8 arranged for abutting against a shoulder 20.5 in the central shaft 20.2 in a manner to prevent the trigger button 20 from being actuated in the as delivered state (see FIG. 9). The retraction sleeve 10 can not translate in proximal direction P due to its proximal end abutting against the stop 2.4. The resilient clips 10.2 may be disengaged from the trigger button 20 by respective bars 9.1 extending distally from the distal end of the plunger 9 upon translation of the plunger 9 in distal direction D. A set of resilient catches 10.3 (shown in FIG. 5B) are arranged on the retraction sleeve 10 proximally from the end face 13 inside the drive spring 8 for engaging respective catches 14.1 extending distally from the decoupling member 14. The catches 14.1 and 10.3 are engaged with each other in a manner to prevent the decoupling member 14 from translating in proximal direction P as long as the trigger button 20 is not pushed. This occurs by respective dogs 20.3 on the proximal end of the trigger button 20 inwardly supporting the catches 10.3 so they cannot flex inwards. The catches 14.1 are outwardly supported by the drive spring 8 so they cannot flex outwards. When the trigger button 20 is actuated the dogs 20.3 are translated in proximal direction P so the catches 10.3 may flex inwards into spaces 20.4 as ramped surfaces of the catches 10.3 and 14.1 slide along each other under load of the drive spring 8.

In order to start an injection the auto-injector 1 has to be pressed against the injection site, e.g. a patient's skin. As a result the interlock sleeve 45 translates in distal direction D into the housing 2 by a small distance taking with it the syringe carrier 7, the syringe 3 with the needle 4, the syringe holder 22 and the plunger 9 until the first shoulder 19 meets the ramped surfaces of the decoupling arms 18. At the same time the clips 45.1 enter a space 2.3 in the housing 2 where they are no longer supported outwardly so they may now flex outwards for decoupling the interlock sleeve 45 from the syringe carrier 7.

When translated into the housing 2 a distal end of the interlock sleeve 45 supports the resilient wedges 10.1 from inside so they cannot be flexed inwards thus preventing the retraction sleeve 10 from translating in distal direction D.

As the plunger 9 translates in distal direction D the bars 9.1 disengage the clips 10.2 so the trigger button 20 becomes unlocked and may now be actuated.

If the auto-injector 1 is removed from the injection site without operating the trigger button 20 the interlock sleeve 45 will translate back into its proximal position under load of the interlock spring 26.

As the trigger button 20 is pushed dogs 20.3 no longer support catches 10.3 and so the catches 10.3 are flexed inwards into the spaces 20.4 as the ramped surfaces of the catches 10.3 and 14.1 slide along each other under load of the drive spring 8. The drive spring 8 now advances the decoupling member 14 and thus the plunger 9 in proximal direction.

The second shoulder 24 pushes the syringe holder 22, syringe carrier 7 and syringe 3 forward while no load is exerted onto the stopper 6. The hollow needle 4 appears from the proximal end P and is inserted into the injection site, e.g. a patient's skin.

The forward movement continues until the syringe holder 22 bottoms out at a first abutment 32 in the housing 2. The travel from the initial position up to this point defines an injection depth, i.e. needle insertion depth.

When the syringe holder 22 has nearly bottomed out the resilient syringe holder arms 23 have reached a widened portion 2.1 of the housing 2 where they are no longer supported by the inner wall of the housing 2. However, since the force required to insert the needle 4 is relatively low the second shoulder 24 will continue to drive forward the syringe holder 22 until proximal travel is halted at the first abutment 32. At this point the syringe holder arms 23 are flexed out by the continued force of the second shoulder 24 and allow it to slip through. Now the plunger 9 no longer pushes against the syringe holder 22 but against the stopper 6 for expelling the medicament M from the syringe 3 and injecting it into or through the patient's skin.

When the stopper 6 has bottomed out in the syringe 3, the retraction sleeve 10 may not yet slide in distal direction D because of the resilient wedges 10.1 being held in the recess 2.2 between the housing 2 and the interlock sleeve 45 as long as the interlock sleeve 45 is in its distal position by the auto-injector 1 being kept pushed against the injection site.

If the auto-injector 1 is taken away from the injection site the interlock sleeve 45 will return to its proximal position (as in FIGS. 3A and 3B) under load of the interlock spring 26 so the resilient wedges 10.1 are no longer supported from inside. Since the drive spring 8 tries to pull the retraction sleeve 10 in distal direction D, distal ramps of the resilient wedges 10.1 move along proximal ramps of the recesses 2.2 thereby flexing the resilient wedges 10.1 inwards as the retraction sleeve 10 starts translating in distal direction D.

The syringe holder 22 is taken along in distal direction D by the retraction sleeve 10, e.g. by a front face 35. Thus the syringe 3 and needle 4 are retracted into a safe position inside the housing 2, e.g. into the initial position. The plunger 9, no longer bearing against the decoupling arms 18 is pulled back too.

The auto-injector 1 of FIGS. 3A and 3B is arranged to retract the syringe 3 and needle 4 at any time during the injection if pulled away from the skin. In FIGS. 1A, 1B, 2A, and 2B, the retraction sleeve held by the interlock sleeve 25 if released before the end of injection will not retract the syringe 3 if the decoupling member 14 does not release the plunger 9 at the same time. The plunger 9 is only released at its end of travel when the decoupling member 14 meets the aperture 34.

Figure 6A:
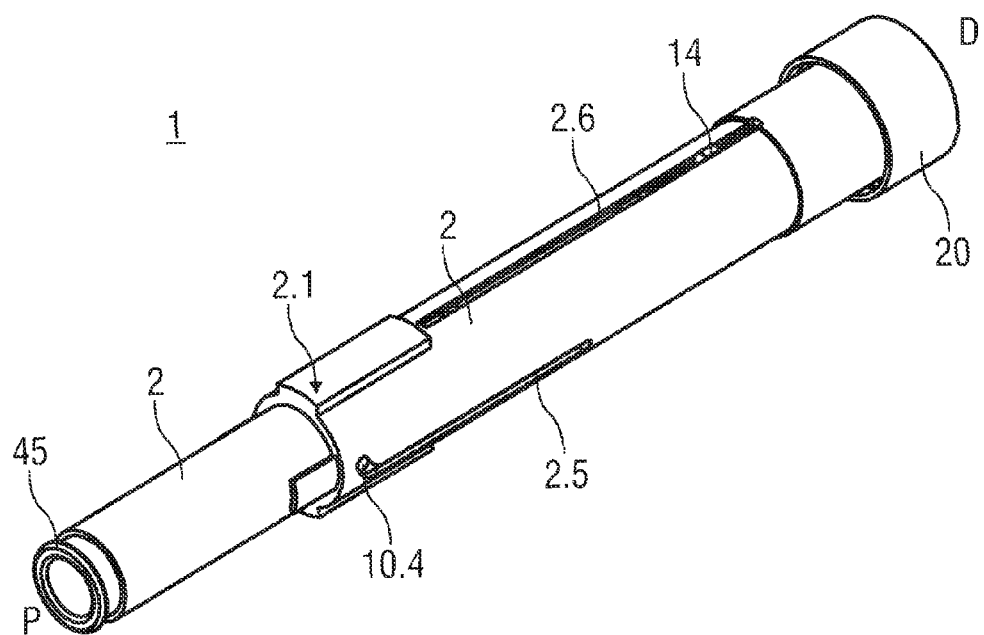
FIGS. 6A and 6B are two isometric views of an embodiment of the auto-injector with the capability to immediately retract the syringe upon removal of the auto-injector from the injection site.
Figure 6B:
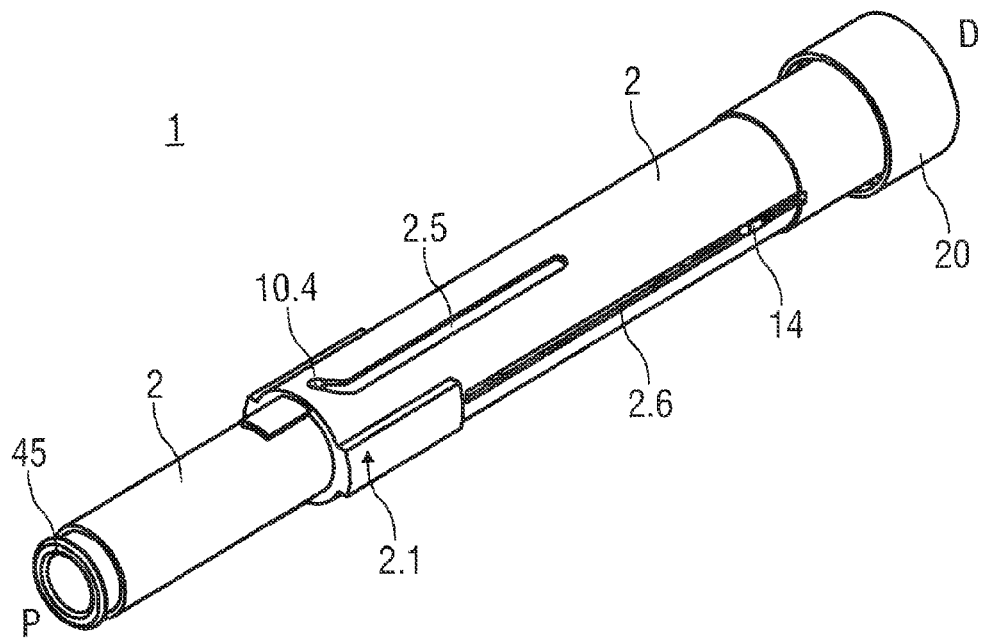

In order to retract the syringe 3 before the end of injection the aperture 34 needs to be available at any time during plunger travel. The aperture 34 therefore extends right to the position of the decoupling arms 18 in the as delivered state. However, the aperture is angularly misaligned with respect to the decoupling arms 18 by a small angle so the decoupling member 14 and the plunger 9 cannot decouple. When the auto-injector 1 is removed from the injection site, the interlock sleeve 45 translates in proximal direction under load of the interlock spring 26 so the resilient wedges 10.1 are no longer supported from inside. Since the drive spring 8 tries to pull the retraction sleeve 10 in distal direction D, distal ramps of the resilient wedges 10.1 move along proximal ramps of the recesses 2.2 thereby flexing the resilient wedges inwards as the retraction sleeve 10 starts translating in distal direction. The retraction sleeve 10 is arranged to rotate in this situation by a small angle thus aligning the aperture 34 and the decoupling arms 18, so the decoupling member 18 decouples from the plunger 9 and the syringe 3 and the needle 4 are retracted into a safe position inside the housing 2. Decoupling part 14 and hence decoupling arms 18 are prevented from rotating in housing 2 by one or more lugs on decoupling member 14 which engage in longitudinal slots 2.6 in housing 2, as shown in FIGS. 6a and 6b. In order to make the retraction sleeve 10 rotate a cam track 2.5 is arranged in the housing 2 and a cam follower 10.4 in the retraction sleeve 10 (see FIGS. 6a and 6b). The cam track 2.5 is essentially parallel to the longitudinal axis of the auto-injector 1 with a short angled section at its proximal end. As long as the cam follower 10.4 runs in the parallel section of the cam track, the retraction sleeve 10 is prevented from rotating.

FIG. 7 shows the auto-injector of FIGS. 3A and 3B with the actuated trigger button 20. FIG. 8 is a cross section in the section plane VIII-VIII illustrating the angular misalignment before the retraction is triggered.

In an alternative embodiment the auto-injector 1 of FIGS. 3A and 3B may have the aperture 34 in the retraction sleeve 10 as in FIGS. 1A, 1B, 2A, and 2B. In this case the needle retraction would occur only at the end of dose.

Likewise, the auto-injector 1 of FIGS. 1A, 1B, 2A, and 2B could be combined with the aperture 34, the cam track 2.5 and the cam follower 10.4 of FIGS. 3 to 8 in order to provide immediate needle retraction at any point during the injection cycle.

The cam track may likewise be arranged in the retraction sleeve 10 and the cam follower in the housing 2.

The housing 2 may have at least one viewing window for inspecting the syringe 3.

The auto-injector 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The aforementioned arrangement for coupling the plunger 9 to either, the syringe 3 or the stopper 6, may be applied in any auto-injector having a plunger for forwarding a force of a drive means to a syringe with a stopper. The primary advantage of this arrangement ensures the load from the drive means is not transferred directly to the stopper until the needle is inserted in the patient, thus avoiding a wet injection. The arrangement comprises the syringe holder 22 and associated syringe holder arms 23, a shoulder (e.g. the second shoulder 24) on the plunger 9, the support of the holder arms 23 by an inner surface in order to prevent them from flexing out in a first position and, a widened portion 2.1 for allowing them to flex radially and to disconnect from the plunger when in a more proximal position. The spring means or other drive means, the ability to retract the syringe or to forward a needle shroud after injection and other features described herein are not required for the prevention of a wet injection.

The invention claimed is:

1. An auto-injector for administering a dose of a liquid medicament, comprising:
    an elongate housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing,
    a retraction sleeve axially movable in the housing between a proximal position and a distal position,
    a single compression spring capable of, upon activation:
        pushing the needle from a covered position inside the housing into an advanced position through the orifice and past the proximal end,
        operating the syringe to supply the dose of medicament, and
        retracting the syringe with the needle into the covered position after delivering the medicament,
    an activator arranged to lock the spring in a pressurized state prior to manual operation and capable of, upon manual operation, releasing the spring for injection,
    wherein a distal end of the spring is arranged to be grounded in the housing such that a proximal end of the spring is configured to move proximally for advancing the needle and for injecting the dose of medicament via a plunger, and the distal end of the spring is releasable from the housing and the proximal end of the spring is configured to be grounded in the housing such that the distal end of the spring is configured to move distally for retracting the syringe,
    further comprising an interlock sleeve telescoped in the proximal end of the housing, the interlock sleeve translatable in longitudinal direction between a proximal position and a distal position and biased in proximal direction in a manner to protrude from the housing in the proximal position,
    wherein the activator comprises a trigger button arranged at the distal end of the auto-injector, the trigger button is locked, thereby preventing actuation when the interlock sleeve is in its proximal position in an as delivered state, and translation of the interlock sleeve unlocks the trigger button so as to allow actuation,
    wherein a cam track is arranged in the housing and a cam follower is arranged in the retraction sleeve, the cam track being essentially parallel to a longitudinal axis of the auto-injector with a short angled section at its proximal end.

2. The auto-injector according to claim 1, wherein in the as delivered state the interlock sleeve is coupled to the plunger for joint axial translation, wherein a distal end of the plunger is arranged to interact with the trigger button in a manner to lock and/or unlock it.

3. The auto-injector according to claim 2, further comprising a tubular syringe carrier for holding the syringe and supporting it at its proximal end, the syringe and the syringe carrier arranged for joint axial translation,
    wherein the syringe carrier is telescoped in the interlock sleeve,
    wherein the syringe is arranged for joint axial translation with a syringe holder provided with at least one resilient syringe holder arm arranged distally, the syringe holder arm having a respective inclined surface for bearing against a second shoulder arranged at the plunger, wherein the syringe holder arm is supportable by an inner surface of the housing in order to prevent it from being flexed outward, and wherein a widened portion is provided in the housing for allowing the syringe holder arm to flex outwards when the syringe holder has nearly reached a maximum proximal position thus allowing the second shoulder to slip past the syringe holder arm and to switch load of the spring from the syringe to the stopper, wherein in its proximal position the interlock sleeve is arranged to be coupled to the syringe carrier in the syringe's retracted position and wherein the interlock sleeve in its distal position is arranged to allow decoupling of the syringe carrier.

4. The auto-injector according to claim 3, wherein the interlock sleeve comprises at least one resilient clip arranged within the housing, wherein a respective recess for each clip is arranged in the syringe carrier so as to allow the clip to engage the syringe carrier, wherein the clip is outwardly supported by the housing in the as delivered state thus preventing it from disengaging the syringe carrier, wherein at least one ramp is arranged to disengage the clip from the recess when the syringe carrier and the interlock sleeve are pushed against each other in longitudinal direction with the interlock sleeve in its distal position.

5. The auto-injector according to claim 2, wherein the spring is arranged inside the retraction sleeve with its distal end bearing against a distal end face and with its proximal end bearing against a thrust face of a decoupling member, wherein in the as delivered state:
   the retraction sleeve is in its proximal position and engaged with the decoupling member so as to prevent release of the spring,
   the trigger button is in its distal position preventing disengagement of the retraction sleeve from the decoupling member,
   the trigger button is latched to the retraction sleeve so as to prevent actuation of the trigger button,
   wherein the plunger is arranged to de-latch the trigger button from the retraction sleeve upon translation of the plunger in distal direction so as to allow actuation of the trigger button, wherein at least one ramp is provided for disengaging the retraction sleeve from the decoupling member under load of the spring when the trigger button is actuated.

6. The auto-injector according to claim 5, wherein a central shaft extends from the trigger button in proximal direction towards the plunger, the central shaft having a shoulder for abutting against at least one resilient clip arranged on the retraction sleeve in the as delivered state, wherein at least one bar extending distally from the distal end of the plunger is arranged to disengage the resilient clip from the central shaft upon translation of the plunger in distal direction.

7. The auto-injector according to claim 5, wherein at least one catch is arranged on the retraction sleeve for engaging a respective catch on the decoupling member in the as delivered state, wherein at least one dog on the trigger button is arranged to support one of the catches prior to actuation of the trigger button so as to prevent disengagement of the catches and wherein the dog is translated upon actuation of the trigger button so as to allow disengagement of the catches.

8. The auto-injector according to claim 5, wherein at least one resilient decoupling arm is arranged at the decoupling member, the decoupling arm having inner ramped surface arranged for bearing against a first shoulder of the plunger in proximal direction, wherein the resilient decoupling arm is supportable by an inner wall of the retraction sleeve in order to prevent the decoupling arm from being flexed outward and slip past the first shoulder and wherein at least one aperture is arranged in the retraction sleeve allowing the decoupling arm to be flexed outward by the first shoulder thus allowing the first shoulder to slip past the decoupling arm in proximal direction.

9. The auto-injector according to claim 8, wherein in the as delivered state the first shoulder is situated a small distance proximally from the ramped surface of the decoupling arm.

10. The auto-injector according to claim 8, wherein the aperture extends at least almost to the position of the decoupling arm in the as delivered state, wherein the aperture is arranged to be angularly misaligned with respect to the decoupling arm when the retraction sleeve is in its proximal position and wherein the aperture is arranged to rotate so as to align with the decoupling arm upon translation of the retraction sleeve out of the proximal position in distal direction.

11. The auto-injector according to claim 5, wherein at least one resilient wedge is arranged at the proximal end of the retraction sleeve, wherein the housing has a respective recess for accommodating the resilient wedge when the retraction sleeve is in its proximal position wherein the interlock sleeve in its distal position is arranged to support the resilient wedge from inside so as to prevent it from translating in distal direction.

12. An auto-injector for administering a dose of a liquid medicament, comprising:
   an elongate housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing,
   a retraction sleeve axially movable in the housing between a proximal position and a distal position,
   a single compression spring capable of, upon activation:
   pushing the needle from a covered position inside the housing into an advanced position through the orifice and past the proximal end,
   operating the syringe to supply the dose of medicament, and
   retracting the syringe with the needle into the covered position after delivering the medicament,
   an activator arranged to lock the spring in a pressurized state prior to manual operation and capable of, upon manual operation, releasing the spring for infection,
   wherein a distal end of the spring is arranged to be grounded in the housing such that a proximal end of the spring is configured to move proximally for advancing the needle and for infecting the dose of medicament via a plunger, and the distal end of the spring is releasable from the housing and the proximal end of the spring is configured to be grounded in the housing such that the distal end of the spring is configured to move distally for retracting the syringe,
   further comprising an interlock sleeve telescoped in the proximal end of the housing, the interlock sleeve translatable in longitudinal direction between a proximal position and a distal position and biased in proximal direction in a manner to protrude from the housing in the proximal position,
   wherein the activator comprises a trigger button arranged at the distal end of the auto-injector, the trigger button is locked, thereby preventing actuation when the interlock sleeve is in its proximal position in an as delivered state, and translation of the interlock sleeve unlocks the trigger button so as to allow actuation,
   wherein a cam track is arranged in the retraction sleeve and a cam follower is arranged in the housing, wherein the cam track is essentially parallel to a longitudinal axis of the auto-injector with a short angled section at its proximal end.

* * * * *